(12) United States Patent
Lee et al.

(10) Patent No.: US 9,383,371 B2
(45) Date of Patent: Jul. 5, 2016

(54) METHOD OF SEQUENTIAL AND MULTIPLE IMMUNOSTAINING FOR DETECTION OF VARIOUS ANTIGENS IN THE SAME SPECIMENS

(71) Applicant: Samsung Electronics Co., Ltd., Suwon-si, Gyeonggi-do (KR)

(72) Inventors: Hun-joo Lee, Hwaseong-si (KR); Jin-ho Oh, Seoul (KR); Jong-myeon Park, Incheon (KR); Yeon-jeong Kim, Yongin-si (KR); Mi-jeong Song, Suwon-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 133 days.

(21) Appl. No.: 13/935,166

(22) Filed: Jul. 3, 2013

(65) Prior Publication Data
US 2014/0120532 A1   May 1, 2014

(30) Foreign Application Priority Data

Oct. 30, 2012   (KR) .................. 10-2012-0121539

(51) Int. Cl.
| | | |
|---|---|---|
| *C12Q 1/68* | (2006.01) |
| *G01N 33/53* | (2006.01) |
| *C12P 19/34* | (2006.01) |
| *G01N 33/00* | (2006.01) |
| *G01N 33/566* | (2006.01) |
| *C07H 21/02* | (2006.01) |
| *A61K 38/00* | (2006.01) |
| *C07K 1/00* | (2006.01) |
| *A61K 39/395* | (2006.01) |
| *A61K 39/00* | (2006.01) |
| *G01N 33/68* | (2006.01) |
| *G01N 33/574* | (2006.01) |

(52) U.S. Cl.
CPC .......... *G01N 33/6893* (2013.01); *G01N 33/574* (2013.01)

(58) Field of Classification Search
USPC ............ 435/6.1, 6.11, 7.1, 91.1; 436/94, 501; 536/23.1, 24.3; 530/300, 350; 424/130.1, 184.1
See application file for complete search history.

(56) References Cited

U.S. PATENT DOCUMENTS

| | | | | |
|---|---|---|---|---|
| 8,865,414 | B2 * | 10/2014 | Hennig et al. ................. | 435/7.1 |
| 2002/0028474 | A1 | 3/2002 | Shibamura et al. | |
| 2005/0090022 | A1 | 4/2005 | Pankowsky | |
| 2006/0063269 | A1 | 3/2006 | Agnew et al. | |

(Continued)

FOREIGN PATENT DOCUMENTS

WO   WO 2008/069973 A2   6/2008

OTHER PUBLICATIONS

The definition of "Immunohistochemistry" from Wikipedia, the free encyclopedia. Printed on May 4, 2015.*

(Continued)

*Primary Examiner* — Frank Lu
(74) *Attorney, Agent, or Firm* — Leydig, Voit & Mayer, Ltd.

(57) ABSTRACT

Provided herein is a method of sequential and multiple immunostaining for detection of various antigens in the same specimens, which may be used for qualitative or quantitative analysis of proteins expressed, gene analysis, and morphological analysis even in specimens where only a small amount is available.

14 Claims, 6 Drawing Sheets
(3 of 6 Drawing Sheet(s) Filed in Color)

(56) References Cited

U.S. PATENT DOCUMENTS

2007/0117102 A1    5/2007    Buzby
2010/0120059 A1    5/2010    Yan et al.
2012/0021439 A1    1/2012    Papin et al.

OTHER PUBLICATIONS

Bai et al., Photocleavage of a 2-nitrobenzyl linker bridging a fluorophore to the 5' end of DNA. PNAS, 100, 409-413, 2003.*

Pirici et al., "Antibody Elution Method for Multiple Immunohistochemistry on Primary Antibodies Raised in the Same Species and of the Same Subtype," *Journal of Histochemistry and Cytochemistry*, 57(6): 567-575 (2009).

Wählby et al., "Multiple Tissue Antigen Analysis by Sequential Immunofluorescence Staining and Multi-Dimensional Image Analysis," *Proceedings of the 12th Scandinavian Conference on Image Analysis (SCIA)*, 25-32 (2001).

European Search Report, European Application No. 13181117.6, dated Nov. 6, 2013.

Blows et al., "Subtyping of Breast Cancer by Immunohistochemistry to Investigate a Relationship between Subtype and Short and Long Term Survival: A Collaborative Analysis of Data for 10,159 Cases from 12 Studies", *PLoS Medicine*, 7(5): e1000279, p. 1-12 (2010).

Chattopadhyay et al., "Quantum dot semiconductor nanocrystals for immunophenotyping by polychromatic flow cytometry", *Nature Medicine*, 12(8): 972-977 (2006).

Coppeta et al., "Dual emission laser induced fluorescence for direct planar scalar behavior measurements", *Experiments in Fluids*, 25: 1-15 (1998).

Sieuwerts et al., "Anti-Epithelial Cell Adhesion Molecule Antibodies and the Detection of Circulating Normal-Like Breast Tumor Cells", *Journal National Cancer Institute*, 101: 61-66 (2009).

Yang et al., "Associations of Breast Cancer Risk Factors With Tumor Subtypes: A Pooled Analysis From the Breast Cancer Association Consortium Studies", *Journal National Cancer Institute*, 103(3): 250-263 (2011).

* cited by examiner

| | Bright field | FITC (Cytkeratin) | Rhodamine (IGFR) |
|---|---|---|---|
| Stain_1 |  |  |  |
| UV_Exposure | |  |  |
| | Bright field | FITC (EpCAM) | Rhodamine (EGFR) |
| Stain_2 |  |  |  |
| UV_Exposure | | | |
| | Bright field | | Rhodamine (HER2) |
| Stain_3 |  | |  | ns.

METHOD OF SEQUENTIAL AND MULTIPLE IMMUNOSTAINING FOR DETECTION OF VARIOUS ANTIGENS IN THE SAME SPECIMENS

CROSS-REFERENCE TO RELATED APPLICATION

This application claims the benefit of Korean Patent Application No. 10-2012-0121539, filed on Oct. 30, 2012, in the Korean Intellectual Property Office, the entire disclosure of which is hereby incorporated by reference.

BACKGROUND

1. Field

The present disclosure relates to a method of sequential and multiple immunostaining for detection of various antigens in the same specimens.

2. Description of the Related Art

In general, cancer diagnosis mainly relies on diagnostic methods based on histopathology. However, these methods have disadvantages that they cannot guarantee to identify any cancer cells present in tissues from which specimens were collected, and also have limitations in accurately identifying the metastasis of a given cancer to another part of a body. Recently, with improved accuracy in cytoscopy a more convenient and accurate diagnosis has been available. Cancer diagnosis may be performed using cells extracted from tissues or those separated from a body fluid such as blood and lymph. However, their lesions are relatively small in size and have a limited number of cells thus limiting the number of tests.

Circulating tumor cells (CTCs) are a type of tumor cells present in a very small amount in the blood of a metastatic cancer patient. CTCs may be discovered from a patient before any tumor is initially detected from the patient. In some cases, CTCs may be also found in cancer patients even after cancer cells have been removed by surgery. Detection, separation, and analysis of separated CTCs are very helpful in early diagnosis of cancers, early diagnosis of cancer metastasis, and prediction of cancer recurrence. However, it is very difficult to accurately analyze the characteristics of the CTCs because they are present only in trace amount and also the cells are very fragile.

In order to detect the presence of cancer cells in a solution, such as blood where various cells with various characteristics are mixed therein, it is necessary to use at least three different kinds of dyes including Cytokeratin, CD45, and nuclear stain. When cells are subject to immunostaining using a dye for color formation or a fluorescent dye there is a limitation in the number of dyes to be used simultaneously. Therefore, there are only a limited number of dyes which may be used for the analysis of genes and proteins of the identified cancer cells. In the related art, when multiple antigen-antibody reactions are performed on the same specimens it usually entails a process of separating antibodies from the antigens. This process may cause temporary modification of protein structure at a condition of very low pH or adjusted ionic concentration, which will damage cells and thereby affect the result of the subsequent tests.

Various tests may be performed using a limited number of specimens in studying the characteristics of cancer cells, providing therapies, selecting therapeutic drugs, and determining prognosis. Therefore, there is a need for the development of a method for testing various antigens using a limited number of specimens without damaging their cells.

SUMMARY

Provided is a method for identifying a target material present in a target cell. The method comprises (i) contacting a dye complex with a sample including the target cell to form a dye-complex-bound target cell, wherein the dye complex comprises (a) a material that binds to the target material, (b) a cleavable linker that is linked to the material that binds to the target material, and (c) a fluorescent dye that is coupled with the cleavable linker; and (ii) measuring a signal from the dye complex-bound target cell.

Provided also is a dye complex comprising (a) a material that binds to a target material, (b) a photocleavable linker linked to the material that binds to the target material, and (c) a fluorescent dye that is coupled with the photocleavable linker.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings.

The patent or application file contains at least one drawing executed in color. Copies of this patent or patent application publication with color drawing(s) will be provided by the Office upon request and payment of the necessary fee.

DETAILED DESCRIPTION

Figure 1:
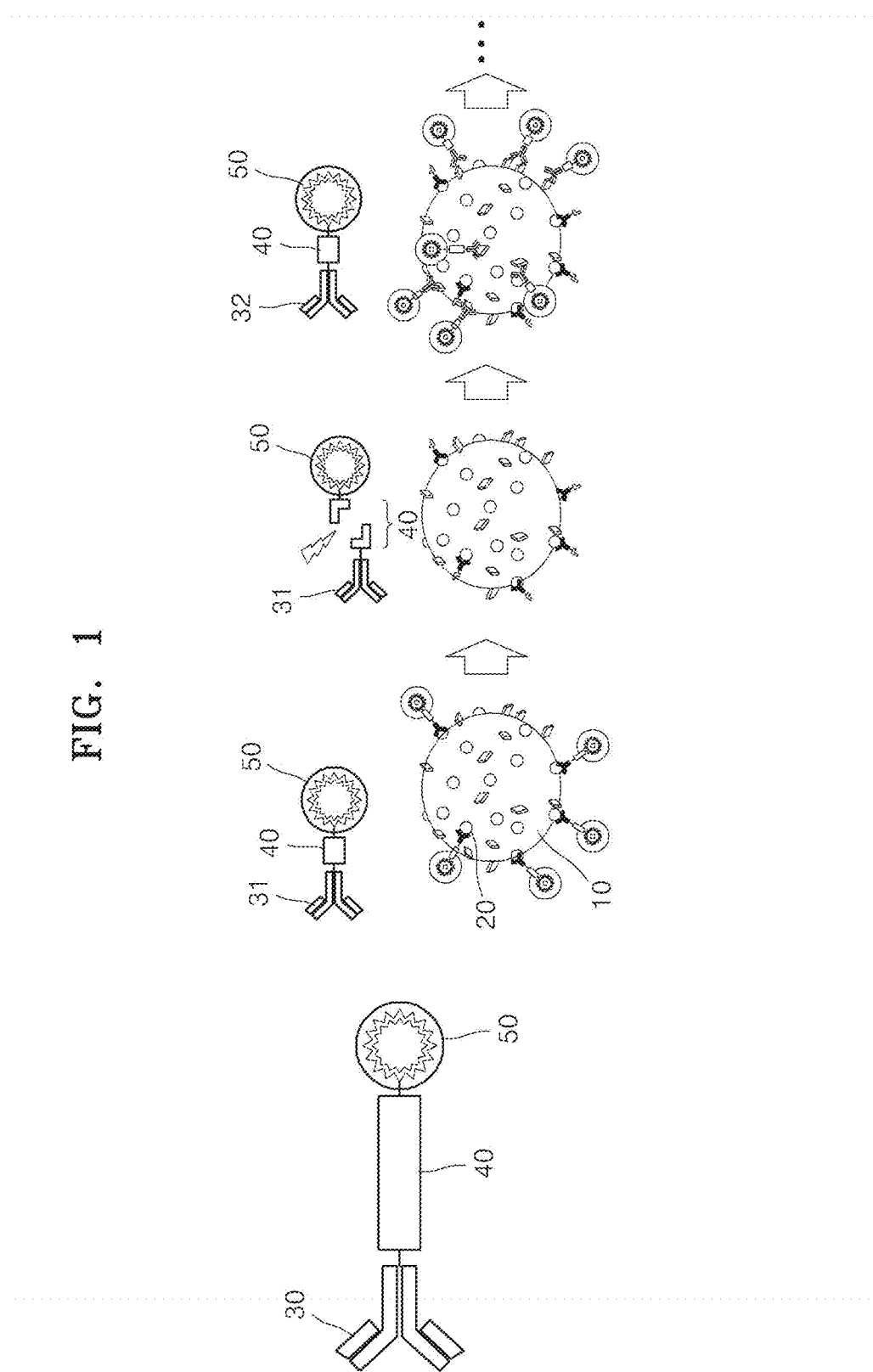
FIG. 1 is a schematic diagram illustrating the constitution of a dye complex and the principle of sequential and multiple immunostaining of cells using the complex.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items.

According to an aspect of the present invention, there is provided a method for identifying target materials present in a target cell. The method comprises contacting a dye complex with a sample including the cell to form a dye complex-bound target cell, and measuring a signal from the dye complex-bound target cell. The dye complex comprises (a) a material that binds to a target material, (b) a photocleavable linker linked to the material that binds to the target material, and (c) a fluorescent dye that is coupled with the photocleavable linker.

The step of contacting a dye complex with a sample including the target cell may be performed under conditions that induce an interaction between a material that binds to the target material and the target material present in the cell included in the sample. For example, the contacting may be performed under conditions that induce specific binding between an antibody and an antigen. Examplary temperatures for the contacting step include 15° C. to 30° C., 18° C. to 27° C., or 20° C. to 25° C. (e.g., 15° C., 16° C., 17° C., 18° C., 19° C., 20° C., 21° C., 22° C., 23° C., 24° C., 25° C., 26° C., 27° C., 28° C., 29° C., or 30° C.). Exemplary pH values for the contacting step include 6 to 8, 6.2 to 7.8, or 6.5 to 7.5.

The dye complex may be a set of a plurality of dye complexes including multiple materials (e.g., antibodies) that bind to the same or different target material and multiple fluorescent dyes. Each fluorescent dye of the plurality of dye complexes may be selected in such a manner that an overlap among emission spectrum of each fluorescent dye is minimized. The number of different dye complexes may be 2 to 20 (i.e., 2, 3, 4, 5, 6, 7, 8, 9, 10, 11, 12, 13, 14, 15, 16, 17, 18, 19, or 20), and prefereably 2, 3, or 4.

The material that binds to the target material in each dye complex may be selected from the group consisting of, for example, an antibody, an antigen, an aptamer, a receptor, a ligand, an enzyme substrate, an enzyme inhibitor, an enzyme cofactor, and an enzyme.

Figure 6:
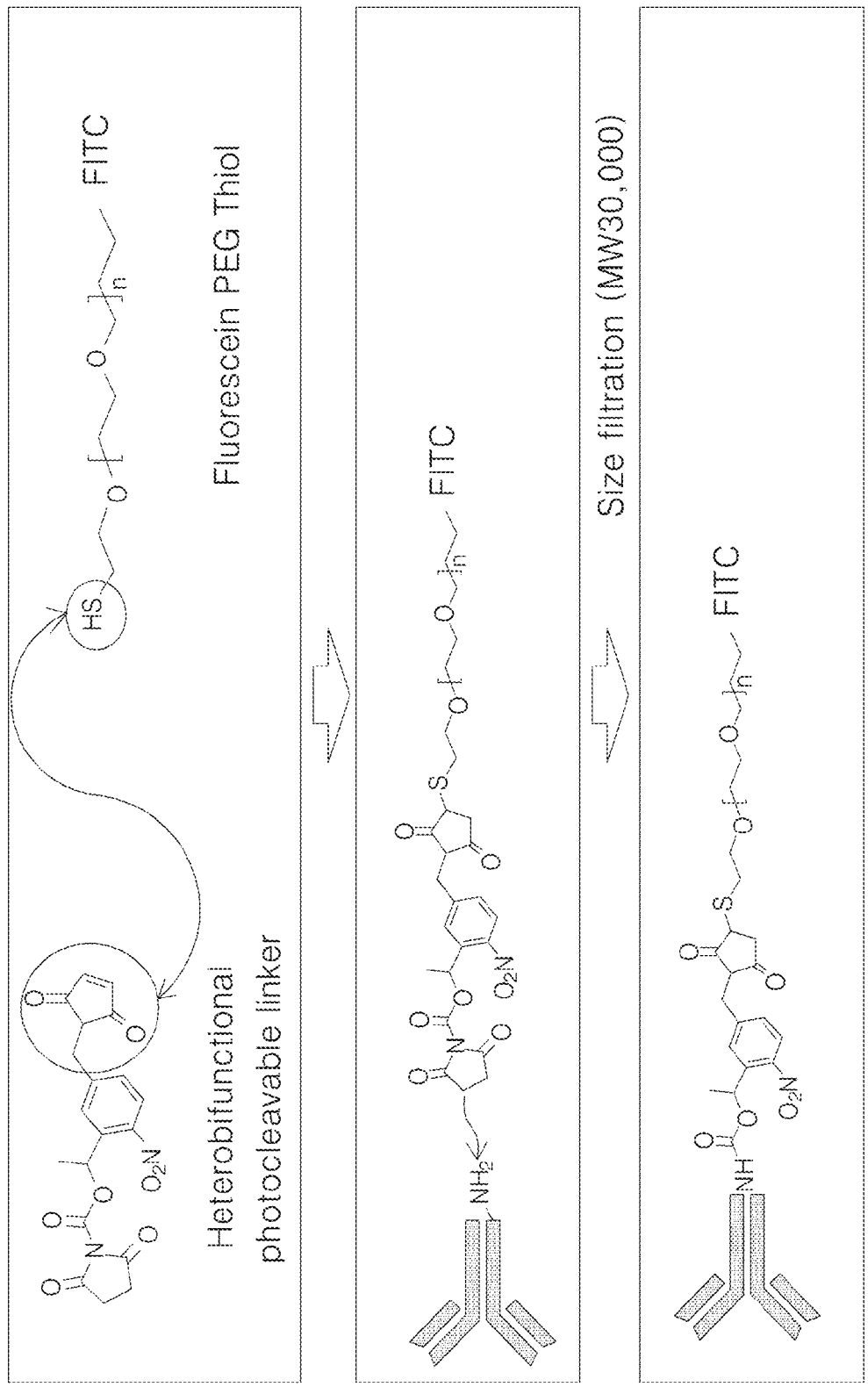
FIG. 6 illustrates a process to prepare an antibody-PC linker-FITC complex. First, 2-methylcyclopent-4-ene-1,3-dione group of heterobifunctional photocleavable linker is conjugated to fluorescein PEG Thiol. Then, pyrrolidine-2,5-dione group of PC linker-FITC is conjugated to amino group of the antibody.

The cleavable linker may be, for example, a photocleavable linker. The photocleavable linker may be cleaved when irradiated with a UV ray or an X-ray. For example, the photocleavable linker may be a compound including a 2-nitrobenzyl group and (coumarin-4-yl)methyl group (see FIG. 6).

The fluorescent dye may be, for example, selected from the group consisting of FITC, Alexa Fluor 488, GFP, CFSE, CFDA-SE, DyLight 488, PE, PI, PerCP, PerCP-Cy5.5, PE-Alexa Fluor 700, PE-Cy5 (TRI-COLOR), PE-Cy5.5, PE-Alexa Fluor 750, PE-Cy7, APC, APC-Cy7, APC-eFluor 780, Alexa Fluor 700, Cy5, Draq-5, Pacific Orange, Amine Aqua, Pacific Blue, DAPI, Alexa Fluor 405, eFluor 450, eFluor 605 Nanocrystals, eFluor 625 Nanocrystals, and eFluor 650 Nanocrystals. In one embodiment, the fluorescent dye may be selected from the group consisting of FITC, DAPI, Cy5, Cy3, Texas Red, and Rhodamine.

Each dye complex may be, for example, one where an antibody is coupled to a fluorescent dye by a photocleavable linker.

The sample may be any biological sample in which a target cell may exist. For example, the sample may be selected from the group consisting of biopsy samples, tissue samples, cell suspensions in which separated cells are suspended in a liquid medium, cell cultures, and a combination thereof. Further, the sample may be isolated from an animal, such as a primate (human), mouse, rat, guinea pig, hamster, rabbit, cat, dog, pig, cow, or horse.

The sample may be an animal body fluid and may be selected from the group consisting of, for example, blood, bone marrow fluid, lymph, saliva, lachrymal fluid, urine, mucosal fluid, amniotic fluid, and a combination thereof. For example, the sample may be blood including circulating tumor cells (CTCs).

The sample may be a cell mixture including different types of cells mixed therein. The mixture may include cells having the target material and other cells that may exist in the biological sample.

The target cell included in the sample may be selected from the group consisting of a circulating tumor cell (CTC), a cancer stem cell, an immune cell, a fetal stem cell, a fetal cell, a cancer cell, and a tumor cell.

The target material present in the cell may be, for example, a material which can distinguish cancer cells from other kinds of cells. For example, the target material may be selected from the group consisting of a protein, a sugar, a lipid, a nucleic acid, and a combination thereof. The target material may be present on the surface or inside a cell. For example, the target material may be a protein, such as cytokeratin present inside a cell, or a cell surface protein such as EpCAM, IGFR, EGFR, and HER2.

The sample, before contacted with a dye complex, may be subject to undergo various steps, for example, fixing a target cell (e.g., by adding chemical fixatives such as aldehydes for crosslinking including paraformaldehyde as described in Example 2, alcohols as precipitating fixatives, oxidizing agents, mercurials, and picrates), increasing cell permeability (e.g., by adding organic solvents, such as methanol and acetone, or detergents such as Triton-X 100 as described in Example 2, saponin, and Tween-20), and/or blocking step to reduce non-specific reactions (e.g., by adding bovine serum albumin as described in Example 2, goat serum, fish skin gelatin, horse serum, swine serum, donkey serum, or rabbit serum).

The measuring step may be a step of measuring the signal generated from the dye complex coupled to the target material present in the cell. The measurement may be, for example, to measure a signal generated by a fluorescent dye of the dye complex under fluorescence microscope. The measuring step, when there is a signal corresponding to the dye complex, among the measured signals, may further include a step of determining that the target material is present in the cell. For example, when there is a signal corresponding to the dye complex that includes a material binding to a cancer-specific marker, the cell may be determined as a cancer cell. Further, the measuring step may be performed after washing off, using a washing solution, the dye complexes which are not specifically bound to the target material in the sample. The washing solution may be, for example, selected from the group consisting of water, a buffer solution (e.g., PBS), a physiological saline, and a combination thereof.

The method may further include a step of irradiating light on the measured specimen to cleave the cleavable linker. The wavelength of the light to be irradiated may vary depending on the type of the linker. For example, the wavelength may be in the range of from about 100 nm to about 600 nm (e.g., 150 nm, 200 nm, 250 nm, 300 nm, 350 nm, 400 nm, 450 nm, 500 nm, or 550 nm), or from about 340 nm to about 370 nm (e.g., 150 nm, 200 nm, 250 nm, 300 nm, 350 nm, 400 nm, 450 nm, 500 nm, or 550 nm), for example, about 365 nm. The irradiation step may be, for example, to separate a part of the linker and the fluorescent dye from the remaining part of the linker and the material that is bound to the target material on the target cell.

In an exemplary embodiment, after the irradiating step, the method may further comprise contacting a dye complex with a sample including a target cell to form a dye-complex-bound target cell, and measuring a signal from the dye complex-bound target cell. In some embodiments, after the irradiating of light is performed, the entire steps of contacting a dye complex with the sample including the target cell to form the dye complex-bound target cell; measuring a signal from the dye complex-bound target cell; and irradiating light on the measured specimen to cleave the cleavable linker, may be sequentially repeated at least once in this order.

The final cycle, for example, may be to perform the contacting step and the measuring step. In other words, after the at least one sequentially repeated cycle, the method may further comprise contacting a dye complex with a sample including a target cell to form a dye-complex-bound target cell, and measuring a signal from the dye complex-bound target cell.

In each cycle, the dye complex that contacts the sample may be a dye complex which is the same or different from the dye complex used in the previous cycle(s). In one embodiment, the dye complex has a material binding to a target material which is different from that in the dye complex used in the previous cycle. For example, a dye complex can include a second antibody having antigen specificity different from a first antibody used in a previous cycle.

The fluorescent dye of a dye complex in each cycle may be the same as or different than the dye included in the dye complex of the previous cycle. Further, the dye complex in each cycle may be a plurality of dye complexes including a different material that binds the same or different target material and a different fluorescent dye. Each fluorescent dye of the plurality of dye complexes may be selected in such a manner that an overlap among emission spectrum of each fluorescent dye is minimized. The number of different dye complexes may be 2 to 20, for example, 2, 3, or 4.

In another exemplary embodiment, after the irradiating step, in situ hybridization or immunohistochemical analysis may be performed in the cell. In situ hybridization may be, for example, to identify the position of a target nucleic acid in a target cell using a fluorescent-labeled nucleic acid probe, for example, fluorescent in situ hybridization (FISH). Immunohistochemical analysis may be, for example, to identify proteins expressed in a target cell via an antigen-antibody reaction.

In a further exemplary embodiment, after the irradiating step, the method may further comprise contacting a dye complex with a sample including a target cell to form a dye-complex-bound target cell, measuring a signal from the dye complex-bound target cell, and irradiating light on the measured specimen to cleave the cleavable linker. In some embodiments, after the irradiating of light is performed, the entire steps of contacting a dye complex with the sample including the target cell to form the dye complex-bound target cell; measuring a signal from the dye complex-bound target cell; and irradiating light on the measured specimen to cleave the cleavable linker, may be repeated at least once in this order, followed by in situ hybridization or immunohistochemical analysis.

In each cycle, the dye complex that contacts the sample may be a dye complex which has a different material binding to a different target material, compared to the previous cycle, for example, a dye complex which includes an antibody having antigen specificity different from that of the previous cycle. The fluorescent dye of a dye complex in each cycle may be the same or different kind of dye included in the dye complex of the previous cycle. Further, the dye complex in each cycle may be a plurality of dye complexes including materials, which are different from each other and respectively bind to different target materials, and fluorescent dyes different from each other.

According to another aspect of the present invention, there is provided a dye complex comprising, consisting essentially of, or consisting of (a) a material that binds to a target material, (b) a photocleavable linker coupled to the material to be bound to the target material, and (c) a fluorescent dye bound to the linker. The material binding to the target material, the photocleavable linker, and the fluorescent dye are described above.

The sequential and multiple immunostaining method according to an aspect of the present invention may be used for the used for qualitative or quantitative analysis, gene analysis, and morphological analysis of proteins expressed in a small amount of specimens.

Example 1

Cancer Cell Labeling Via Antibody-Photocleavable (PC) Linker-Complex

10 µL of self-manufactured 50 nmol heterobifunctional photocleavable linker (Chemical formula shown below) in DMF and 15 µL of 50 nmol dye solution (Fluorescein PEG Thiol (MW 5000), Rhodamine PEG Thiol, (MW 5000), Nanocs Inc.) in phosphate buffer (50 mM, pH 5) were reacted at room temperature for 30 minutes.

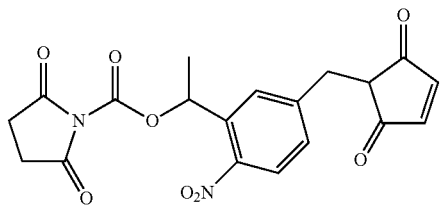 [SMILES: CC(OC(=O)N1C(=O)CCC1=O)c1cc(CC2C(=O)C=CC2=O)ccc1[N+](=O)[O-]]

100 µL of 10 nmol anti-cytokeratin 7,8,18 antibody or anti-EpCAM antibody in 1× PBS solution was added, and the mixture was reacted overnight at 4° C. Then, unreacted dyes were removed using Amicon® Ultra centrifugal filter (Millipore, MW 30,000) and the resulting product was concentrated 5-fold. 5 µL of the obtained antibody-PC linker-complex was added to a PBS buffer solution with 1% BSA. The mixture was added to SK-BR3 breast cancer cells and stirred at 15 rpm for 1 hour. Binding between SK-BR3 and the complex was confirmed by fluorescence microscope (Olympus IX81).

Figure 2:
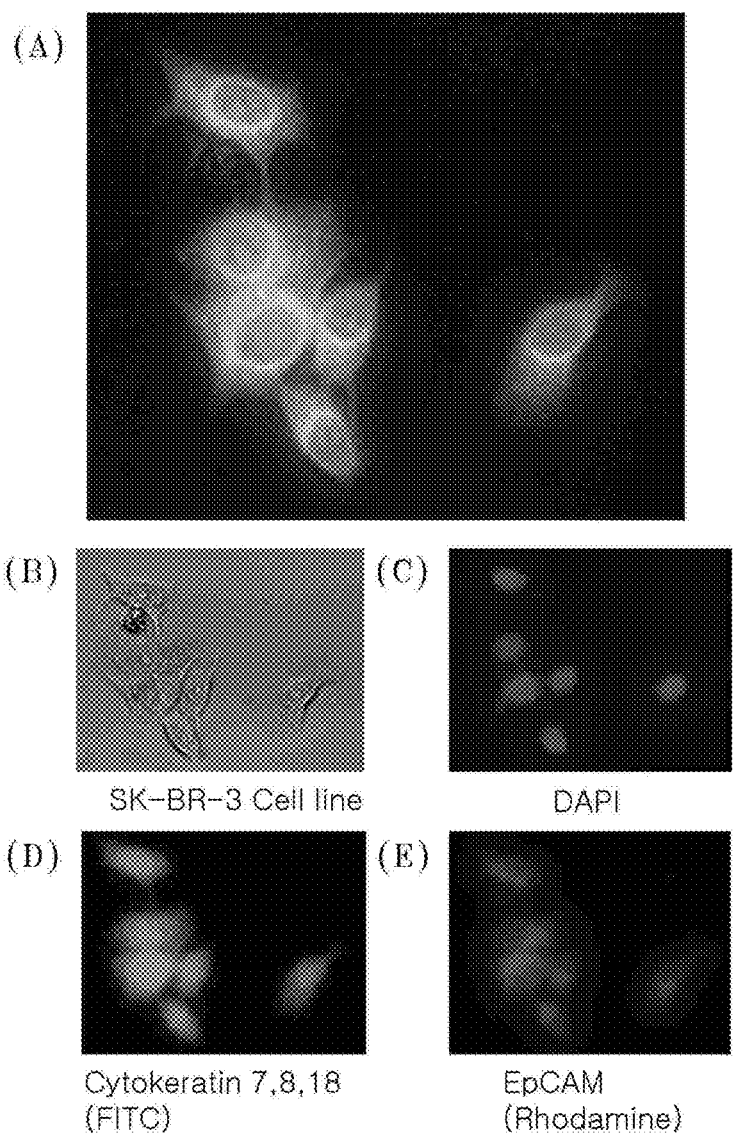
FIG. 2A shows a merged image of FIGS. 2C-E.
FIG. 2B shows an image of SK-BR3 before staining.
FIG. 2C shows a DAPI fluorescence image of SK-BR3 that is not bound with the complex of FIG. 1.
FIGS. 2D and 2E show a fluorescence image of SK-BR3 that is bound with an anti-cytokeratin 7,8,18 antibody-PC linker-FITC complex, and a fluorescence image of SK-BR3 that is bound with an anti-EpCAM antibody-PC linker-Rhodamine complex, respectively.

FIG. 2A shows a merged image of FIGS. 2C-E. FIG. 2B shows an image of SK-BR3 before staining. FIG. 2C shows a DAPI fluorescence image of SK-BR3 to which a complex is not bound. FIGS. 2D and 2E show a fluorescence image of SK-BR3 to which anti-cytokeratin 7,8,18 antibody-PC linker-FITC complex is bound; and a fluorescence image of SK-BR3 to which anti-EpCAM antibody-PC linker-Rhodamine complex is bound, respectively. It was confirmed that cancer cells were labeled by the complex added therein.

Example 2

Verification of Dye Dissection According to Light Exposure

BT474 breast cancer cells were fixed with 4% paraformaldehyde solution for 10 minutes and then treated with 0.2% Trition-X 100 for 10 minutes to increase permeability of the cells. After adding 1% BSA solution, the cells were stained with an anti-cytokeratin antibody-PC linker-FITC complex or anti-IGFR antibody-PC linker-Rhodamine complex at room temperature for 60 minutes. Then, the cells were washed with 1×PBS and observed under fluorescence microscope while increasing the intensity of irradiation (J) of light at a wavelength of 365 nm.

Figure 3:
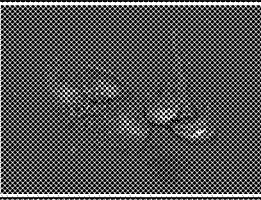
FIG. 3 shows the change in fluorescence signal of FITC and Rhodamine dyes bound to BT474 breast cancer cells according to light exposure.

FIG. 3 shows the change in fluorescence signal of FITC and Rhodamine dyes bound to BT474 breast cancer cells according to light exposure. It was confirmed that as the intensity of irradiation increased, the intensity of fluorescence signal decreased and, thus, the ratio of dye being removed increased.

Example 3

Staining of Reset Cells

SK-BR3 breast cancer cells were fixed with 4% paraformaldehyde solution for 10 minutes and then treated with 0.2% Trition-X 100 for 10 minutes to increase permeability of the cells. After adding 1% BSA solution, the cells were stained with an anti-cytokeratin antibody-PC linker-FITC complex or anti-IGFR antibody-PC linker-Rhodamine complex at room temperature for 60 minutes. Then, the cells were washed with 1×PBS, exposed to light (20 J) at 365 nm, and then respectively stained with anti-EpCAM antibody-PC linker-FITC complex or anti-EGFR antibody-PC linker-Rhodamine complex at room temperature for 60 minutes, and the intensity of fluorescence signal was measured according to each dye complex. The cells in the control group were subject to the same process as described above in regard to fixing the cells, increasing permeability of the hcells, and BSA blocking, followed by staining the cells with an anti-EpCAM antibody-PC linker-FITC complex or anti-EGFR antibody-PC linker-Rhodamine complex, respectively, at room temperature for 60 minutes, and measuring intensity of fluorescence signal of the cells according to each dye complex.

Figure 4:
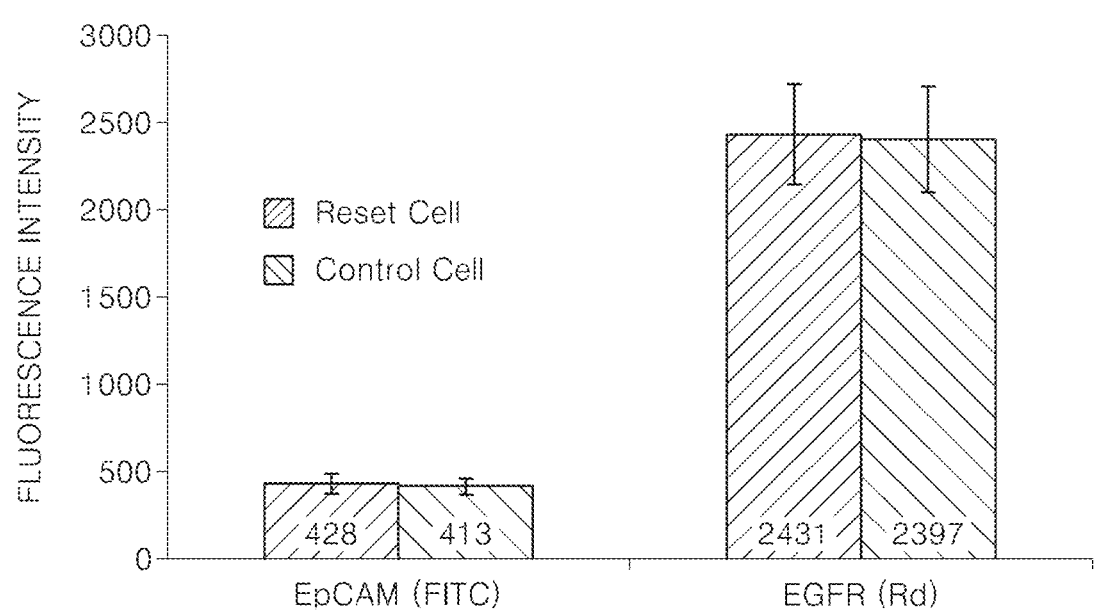
FIG. 4 shows the result of quantitatively comparing staining efficiency of cells which were subject to a primary staining followed by light exposure and a secondary staining. Control cells were subject to only a primary staining. Fluorescence intensity I indiated on the y-axis.

FIG. 4 shows the result of quantitatively comparing the staining efficiency between the cells which were subject to a primary staining followed by light exposure and a secondary staining, and the control cells which were subject to only a primary staining. When the cells were stained with either anti-EpCAM antibody-PC linker-FITC complex or anti-EGFR antibody-PC linker-Rhodamine complex, the intensity of fluorescence signal of cells which underwent a secondary staining after the primary staining showed an equal level of intensity within an error range to that of cells that underwent only the primary staining, thus confirming that light exposure did not affect the staining of cells.

Example 4

Five Different Types of Antigen Test Using Sequential and Multiple Cell Staining SK-BR3 breast cancer cells were fixed with 4% paraformaldehyde solution for 10 minutes, and treated with 0.2% Trition-X 100 for 10 minutes to increase the permeability of the cells. After adding 1% BSA solution, the cells were stained (as a primary staining) with anti-cytokeratin antibody-PC linker-FITC complex and anti-IGFR antibody-PC linker-Rhodamine complex at room temperature for 60 minutes, and then washed with 1×PBS. The cells were then exposed to light at 365 nm (20 J), and stained (as a secondary staining) with anti-EpCAM antibody-PC linker-FITC complex and anti-EGFR antibody-PC linker-Rhodamine complex at room temperature for 60 minutes. The cells were washed again with 1×PBS, exposed to light at 365 nm (20 J), and stained (as a tertiary staining) with anti-HER2 antibody-PC linker-Rhodamine complex at room temperature for 60 minutes. The cells after the primary, secondary and tertiary staining and exposure to light were observed under fluorescence microscope.

Figure 5:
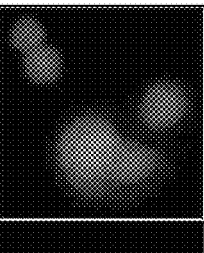
FIG. 5 shows the result of identifying the expression of five different types of antigens in SK-BR3 breast cancer cells via three cycles of sequential staining processes.
Figure 5:
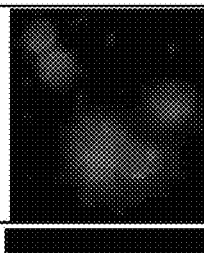
Figure 5:
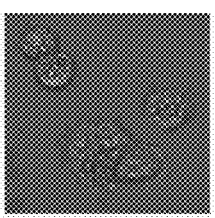
Figure 5:
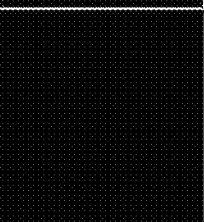
Figure 5:
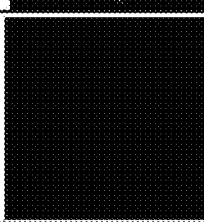
Figure 5:
Figure 5:
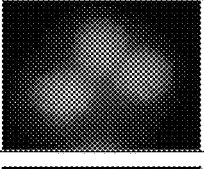
Figure 5:
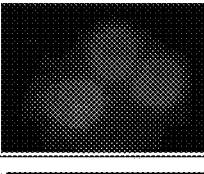
Figure 5:
Figure 5:
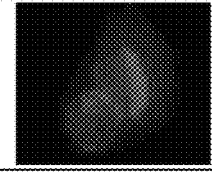

FIG. 5 shows the result of identifying the expression of 5 different types of antigens in SK-BR3 breast cancer cells via three cycles of sequential staining processes.

While an exemplary embodiment of the present invention has been described in detail, the protection scope of the present invention is not limited to the foregoing embodiment and it will be appreciated by those skilled in the art that various modifications and improvements using the basic concept of the present invention defined in the appended claims are also included in the protection scope of the present invention.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for identifying a target material in or on a cell, comprising:
   contacting a dye complex with a sample including the cell and forming a dye-complex-bound cell, wherein the dye complex comprises (a) a material that binds to the target material, (b) a photocleavable compound that is linked to the material that binds to the target material, and (c) a fluorescent dye that is coupled with the photocleavable compound; and
   measuring a signal from the dye complex-bound target cell, thereby identifying the target material in or on the cell, wherein the photocleavable compound is

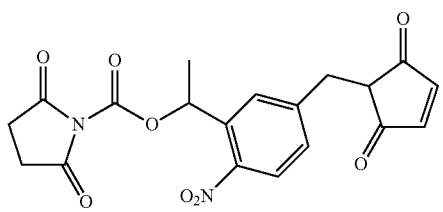 [SMILES: CC(OC(=O)N1C(=O)CCC1=O)c1cc(CC2C(=O)C=CC2=O)ccc1[N+](=O)[O-]]

which is linked to the material that binds to the target material and coupled to the fluorescent dye.

2. The method of claim 1, wherein the material that binds to the target material is an antibody, an antigen, an aptamer, a receptor, a ligand, an enzyme substrate, an enzyme inhibitor, an enzyme cofactor, or an enzyme.

3. The method of claim 1, wherein the fluorescent dye is FITC, DAPI, Cy5, Cy3, Texas Red, or Rhodamine.

4. The method of claim 1, wherein the target material is a protein, a sugar, a lipid, a nucleic acid, or a combination thereof.

5. The method of claim 1, wherein the target cell is a circulating tumor cell, a cancer stem cell, an immune cell, a fetal stem cell, a fetal cell, a cancer cell, or a tumor cell.

6. The method of claim 1, further comprising irradiating light on the dye complex-bound cell to cleave the photocleavable compound.

7. The method of claim 6, further comprising, after said irradiating light on the dye complex-bound cell, contacting another dye complex with sample including the cell and forming another dye-complex-bound cell, and measuring a signal from the another dye complex-bound cell.

8. The method of claim 6, further comprising, after said irradiating light on the dye complex-bound cell,
   at least one sequential cycle including contacting another dye complex with the sample including the cell and forming another dye-complex-bound cell, measuring a signal from the another dye complex-bound cell, and irradiating light on the another dye complex-bound cell.

9. The method of claim 8, further comprising performing in situ hybridization or immunohistochemical analysis on the cell after the irradiation step of the at least one sequential cycle.

10. The method of claim 9, wherein the another dye complex in each sequential cycle of the at least one sequential cycle comprises a material binding to a target material and the material binding to the target material is different from the material in the dye complex of claim 1.

11. The method of claim 8, wherein the another dye complex in each sequential cycle of the at least one sequential cycle comprises a material binding to a target material and the material binding to the target material is different from the material in the dye complex of claim 1.

12. The method of claim 11, wherein the another dye complex in each sequential cycle of the at least one sequential cycle binds a target material that is different from the target material in the dye complex of claim 1.

13. The method of claim 11, wherein, comparing with the dye complex in claim 1, the another dye complex in each sequential cycle of the at least one sequential cycle binds the target material with a different specificity.

14. The method of claim 6, further comprising performing in situ hybridization or immunohistochemical analysis on the cell after said irradiating light on the dye complex-bound cell.

* * * * *